United States Patent [19]
Newnham

[11] 4,440,760
[45] Apr. 3, 1984

[54] FOOD SUPPLEMENT

[76] Inventor: Rex E. Newnham, 144 Collins St., Thornbury, Australia, 3071

[21] Appl. No.: 287,235

[22] Filed: Jul. 27, 1981

[51] Int. Cl.$^3$ .......................................... A61K 31/695
[52] U.S. Cl. .................................................. 424/184
[58] Field of Search ........................................ 424/184

Primary Examiner—Stanley J. Friedman
Attorney, Agent, or Firm—Christie, Parker & Hale

[57] ABSTRACT

There is provided a composition for relief and treatment of arthritic conditions which comprises from 2 to about 500 parts by weight of a boron-containing compound, the herbs Guaiacum, Berberis and Harpagophytum recumbens, each in an amount up to an equivalent of 150 parts by weight of the dried herb. Rhus-tox and Bryonia are present. The compositions includes excipients and fillers.

14 Claims, No Drawings

FOOD SUPPLEMENT

BACKGROUND OF THE INVENTION

The present invention relates to food-supplement compositions for alleviating the discomforts of arthritis, including rheumatoid arthritis and osteoarthritis.

It is believed that the onset of arthritis is, at least in part, due to a mineral deficiency in boron and, to a lesser extent, magnesium. Close analysis of the food intake of arthritis-sufferers suggests this to be the case, and treatment with a mixture of boron- and magnesium-containing compounds supports this finding. Such is described in Australian Patent No. 514,161, issued to me on the May 8, 1981.

The patent describes a composition comprising an inorganic boron-containing compound in combination with an inorganic magnesium-containing compound as utile for treating arthritic conditions when orally administered.

SUMMARY OF THE INVENTION

According to the present invention, there is provided a composition, normally in tablet form, comprising from about 2 to about 500 parts by weight of a boron-containing compound, preferably sodium tetraborate decahydrate; quaiacum in an amount up to the equvalent of 150 parts by weight of the dried herb; berberis in an amount up to the equivalent of 150 parts by weight of the dried herb; harpagophytum recumbens in an amount up to the equivalent of 150 parts by weight of the dried herb; the balance of the composition being substantially excipients and fillers.

Excipients are a combination of one or more ingredients used to bind the composition together, to enable rapid dissolution of the ingredients when ingested, and to lubricate the composition during molding the composition into a tablet or the like. The usual excipient ingredients are gum arabic, starch, and magnesium stearate. Fillers, which may be present, may be functional, such as a magnesium compound, such as magnesium phosphate, magnesium oxide, magnesium carbonate and the like; as well as inerts, such as lactose, calcium carbonate and the like. Additional functional ingredients present in the composition are Rhus-tox and Bryonia, individually or in combination; mixtures are preferred. They are present in small but effective amounts, usually less than about 1 ppm each based on the total weight of the composition as measured in milligram quantities.

DETAILED DESCRIPTION

According to the present invention, there is provided a new and novel composition for relief and treatment of arthritic conditions in animals. The composition provided in accordance with the present invention contains from about 2 to about 500 parts by weight of a boron-containing compound, preferably sodium tetraborate decahydrate, although boric acid may also be used; up to about 150 parts by weight of the dried herb quaiacum, preferably from 1 to about 150 parts by weight; up to about 150 parts by weight of the dried herb berberis, preferably from 1 to about 150 parts by weight; and up to about 150 parts by weight of the dried herb *Harpagophytum recumbens*, preferably from 1 to about 150 parts by weight. Other herbs may also be included, and the effective ingredient of the herb by means of solvent addition.

Also included in the composition is a filler which includes an excipient. An excipient is a composition of one or more ingredients which serve to bind the constituents of the composition together, to enable them to be rapidly dissolved on ingestion, and as a lubricant in molding tablets. Fillers may be functional, such as magnesium phosphate, magnesium oxide, magnesium carbonate and the like; or inerts, such as lactose, calcium carbonate and the like. Normally, the amount of excipient present will range from about 40 to about 100 parts by weight, typically about 55 to 65 parts by weight, and the amount of fillers employed is in an amount sufficient to provide a tablet of desired weight. The typical ingredients of an excipient are including a first ingredient gum arabic, which serves as the binder; magnesium stearate, a third ingredient which serves as the mold lubricant; and starch, a second ingredient which enables rapid disintegration of the composition upon ingestion. Normally, the amounts of the various ingredients are provided in milligram quantities.

The pharmaceutical composition is normally provided in a dry form. The guaiacum, berberis and harpagophytum recumbens may be provided as a fluid extract, and the fluid carrier for the extract evaporated from the solids to leave an equivalent amount of the functional ingredient of the dried herb. Moist herbs may also be used but add to the cost of providing a dry composition.

To the composition there is provided Rhus-tox and Bryonia, each in amounts effective for their respective purposes. Rhus-tox is a homeopathic substance effective for the relief of arthritic attacks which occur after periods of rest. Bryonia is a homeopathic substance which is effective in relief of arthritic attacks after periods of activity. Both are added to the dry ingredients of the composition as a 6× solution and the solvent evaporated, leaving the effective ingredients in a concentration up to about 1 ppm based on the total weight of the composition.

The following is a presently preferred composition for tablets weighing about 500 mg:

| | |
|---|---|
| Sodium tetraborate decahydrate | 24 mg |
| Guaiacum | 25 mg |
| Berberis | 25 mg |
| Harpagophytum recumbens | 25 mg |
| Excipient | 60 mg |
| Filler | Balance to make 500 mg |
| Rhustox | <1 ppm |
| Bryonia | <1 ppm |

The solids are inpregnated with a 6× solution of Rhustox and a 6× solution of Bryonia, evaporated and dried. The composition, normally in tablet form, is administered orally, typically to provide a dosage of from 50 to 100 mg of the boron-containing compound. Daily dosages may range from as little as 25 mg to 3,000 mg of the boron-containing compound, preferably in the range of from 50 to 100 mg.

When administered to animals, sheep and goats would normally receive the same dosage as humans. Cattle, on the other hand, would be administered dosages in the amount of 25 mg of the boron-containing compound per 60 kg of body weight. With cattle, the solids are normally fixed with a chaff or other feed.

Variations and modifications may be made to the aforementioned compositions, including the addition of other herbs, without departing from the spirit and scope of the invention.

What is claimed is:

1. A composition useful for the treatment of arthritis which comprises from about 2 to about 500 parts by weight of a boron-containing compound; Guaiacum in an amount up to an equivalent of 150 parts by weight of the dried herb; Berberis in an amount up to an equivalent of 150 parts by weight of the dried herb; Harpagophytum recumbens in an amount up to an equivalent of 150 parts by weight of the dried herb; and an effective amount of a compound selected from the group consisting of Rhus-tox, Bryonia, or mixtures thereof.

2. A composition as claimed in claim 1 in which there is provided an excipient including a first ingredient for binding the composition into a tablet; a second ingredient for disintegrating the tablet on ingestion; and a third ingredient for lubricating the composition for pressing into a tablet.

3. A composition as claimed in claim 2 in which the first ingredient is gum arabic; the second ingredient is starch; and the third ingredient is magnesium stearate.

4. A composition as claimed in claim 1, 2 or 3 which includes a filler.

5. A composition as claimed in claim 1, 2 or 3 in which the excipient is present in an amount of from about 40 to about 100 parts by weight.

6. A composition as claimed in claim 1, 2 or 3 in which the boron-containing compound is sodium tetraborate decahydrate.

7. A composition as claimed in claim 1 in which Rhustox and Bryonia are each present in an amount up to about 1 ppm based on the total weight of the composition.

8. A composition as claimed in claim 1 in which Guaiacum is present in an amount equivalent to from about 1 to about 150 parts by weight of the dried herb; Berberis is present in an amount equivalent to from about 1 to about 150 parts by weight of the dried herb; Harpagophytum recumbens is present in an amount equivalent to from about 1 to about 150 parts by weight of the dried herb; and in which the composition contains 55 to 65 parts by weight excipient.

9. A tablet comprising about 25 milligrams sodium tetraborate decahydrate; about 25 milligrams of the dried herb Guaiacum; about 25 milligrams of the dried herb Berberis; about 25 milligrams of the dried herb Harpagophytum recumben; from about 40 to about 100 milligrams of an excipient comprising gum arabic, starch and magnesium stearate; and filler sufficient to provide a tablet weighing about 500 milligrams and in which Rhustox is present in an amount less than 1 ppm and in which Bryonia is present in an amount less than about 1 ppm.

10. A tablet as claimed in claim 9 in which the excipient is present in an amount of from about 55 to about 65 milligrams.

11. A process for forming a pharmaceutical composition which comprises:

(a) blending solids comprising from 2 to about 500 parts by weight of boron-containing compound; the equivalent of from 1 to about 150 parts by weight of the dried herb Guaiacum; the equivalent of from 1 to about 150 parts by weight of the dried herb Berberis; the equivalent of from 1 to about 150 parts by weight of the dried herb Harpagophytum recumbens; and from 40 to about 100 parts by weight of an expectorant comprising gum arabic, starch and magnesium carbonate; and (b) impregnating the solids with a 6× solvent solution of Rhustox and a 6× solvent solution of Bryonia, in a quantity sufficient to provide up to 1 ppm per weight each of Rhustox and Bryonia based on the total weight of the composition upon evaporation of the solvent for Rhustox and the solvent for Bryonia.

12. A process as claimed in claim 11 in which the boron-containing compound is sodium tetraborate decahydrate.

13. A composition as claimed in claim 4 in which the boron-containing compound is sodium tetraborate decahydrate.

14. A composition as claimed in claim 5 in which the boron-containing compound is sodium tetraborate decahydrate.

* * * * *